United States Patent [19]

Gazzano

[11] Patent Number: 5,112,370
[45] Date of Patent: May 12, 1992

[54] DEVICE FOR STERILIZING A FORCED AIR FLOW BY MEANS OF ULTRAVIOLET RADIATIONS

[76] Inventor: Michele Gazzano, Via Alessi 15, 20123 Milan, Italy

[21] Appl. No.: 740,863

[22] Filed: Jul. 31, 1991

Related U.S. Application Data

[63] Continuation-in-part of Ser. No. 615,215, Nov. 19, 1990, abandoned.

Foreign Application Priority Data

Dec. 13, 1989 [IT] Italy ................. 22682 A/89

[51] Int. Cl.⁵ ............................. B03C 3/38
[52] U.S. Cl. ......................... 55/102; 55/279; 422/121
[58] Field of Search ............ 55/102, 249, 385.3; 422/24, 121

[56] References Cited

U.S. PATENT DOCUMENTS

| | | | |
|---|---|---|---|
| 3,043,977 | 7/1962 | Morowitz | 422/121 X |
| 3,313,971 | 4/1967 | Nagy | 422/121 X |
| 3,674,421 | 7/1972 | Decuppes | 422/121 |
| 3,846,070 | 11/1974 | Patterson | 422/121 |
| 4,118,191 | 10/1978 | Bohnensieker | 55/279 |
| 4,245,550 | 1/1981 | Suzuki et al. | 55/102 X |
| 4,990,313 | 2/1991 | Pacosz | 422/121 |

*Primary Examiner*—Charles Hart
*Attorney, Agent, or Firm*—Synnestvedt & Lechner

[57] ABSTRACT

A device for sterilizing a forced air flow by means of ultraviolet radiations, comprising an elongated housing provided with reflecting inner surfaces accomodating at least an ultraviolet radiations source and a fan for sucking air into the device and sending it out after being subjected to the ultraviolet radiation in an air flow passage.

The device provides at each ends means for shielding and absorbing the ultraviolet radiation to prevent the dispersion thereof outside the device, made up by an optical labyrinth formed by parallel and spaced fins.

In an embodiment to be applied to an air conditioning plant, the device does not include a fan and the input opening is shaped for being fitted the output of an air conditioning duct.

9 Claims, 4 Drawing Sheets

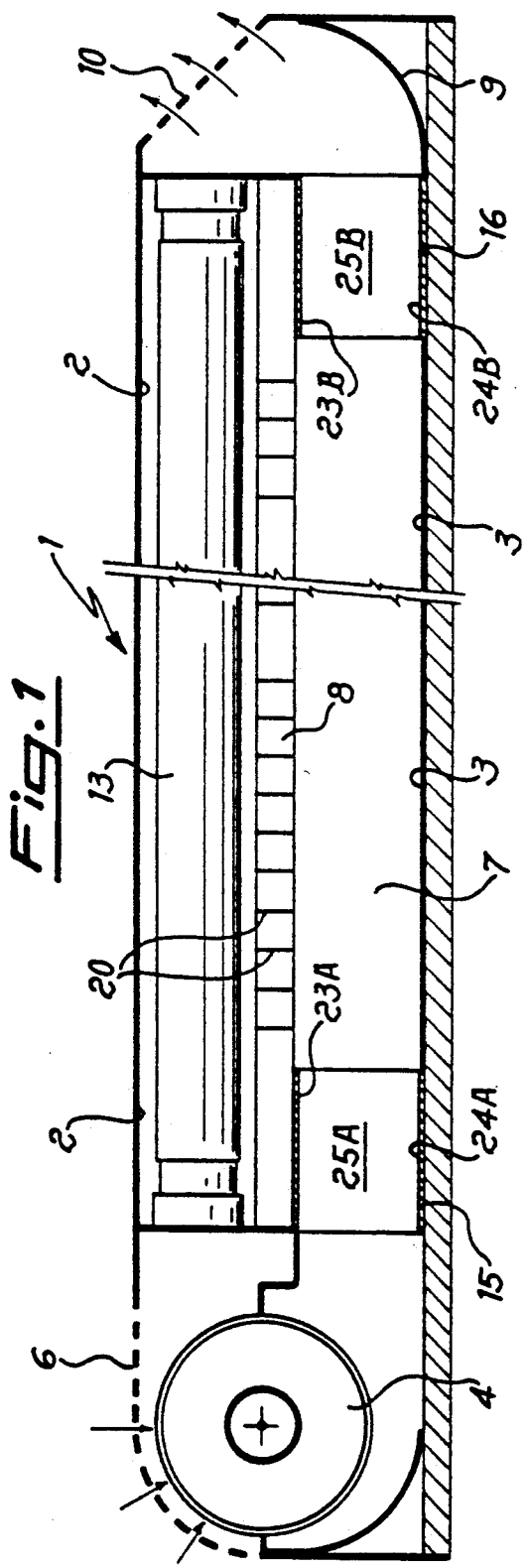
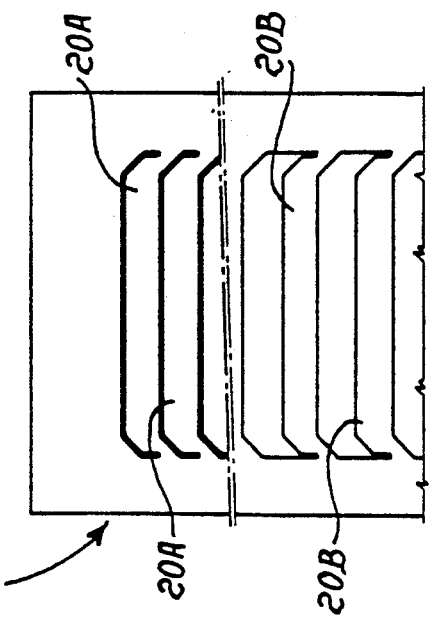
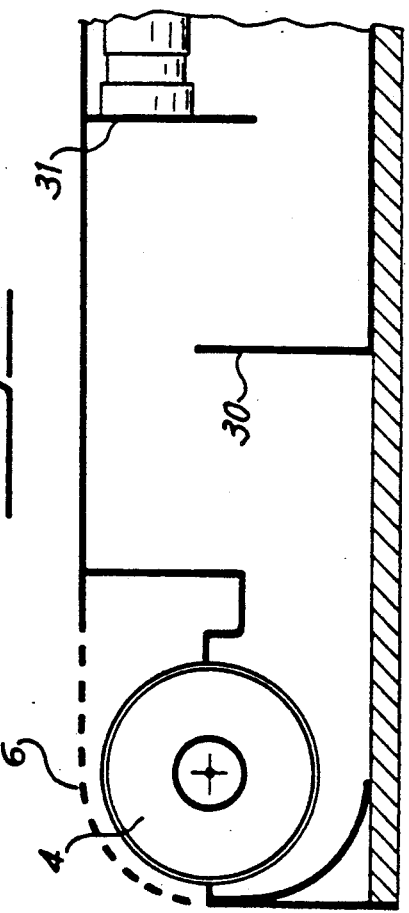

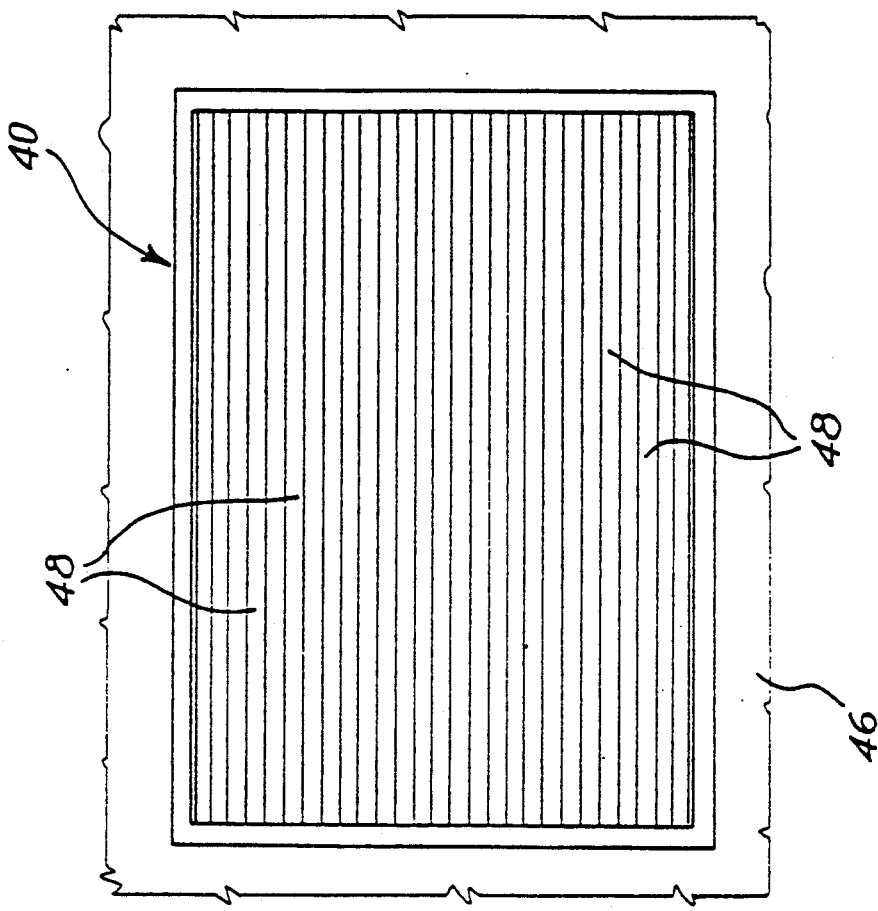
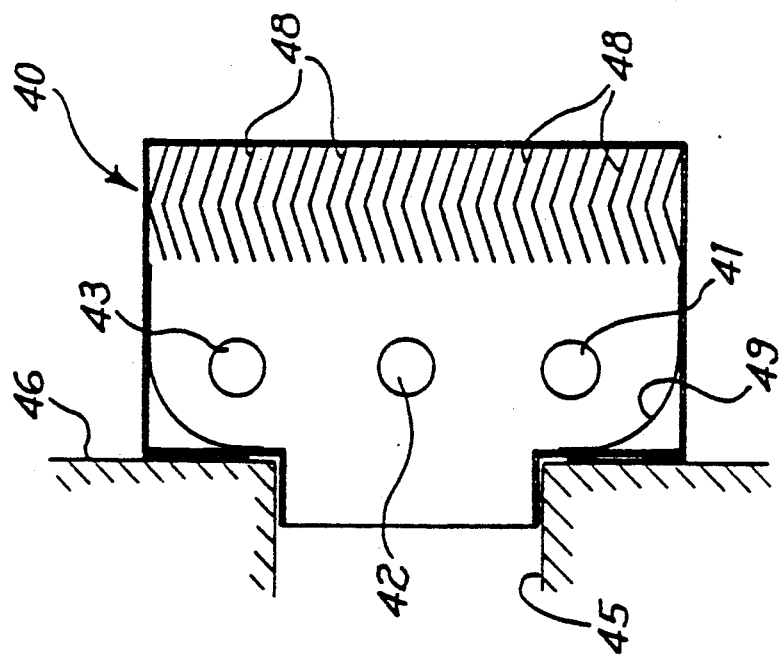

5,112,370

DEVICE FOR STERILIZING A FORCED AIR FLOW BY MEANS OF ULTRAVIOLET RADIATIONS

This is a continuation-in-part of copending application Ser. No. 07/615,215 filed on Nov. 19, 1990, now abandoned.

BACKGROUND OF THE INVENTION

The present invention relates to an apparatus for sterilising the air of rooms and the like by means of ultraviolet radiations, and more particularly of those ultraviolet radiations known as UV-C (short waves) having a wavelenght between 100 and 280 nanometers.

The sterilising and bactericide action of these radiations is used not only for the disinfection of public and private premises, particularly hospitals and nursing homes, but even in rooms opened to the public and also in homes for hygienic and prevention purposes.

The known devices provide for the use of low pressure mercury vapor lamps as sources of the ultraviolet radiation, which are directed upward and laterally shielded since the direct exposition to this particular radiation is harmful to the persons.

Altough this type of radiation is easily absorbed by properly treated surfaces, e.g. subjected to an oil painting, nevertheless there is a risk of people being radiated by the dispersed radiations or the reflected fraction if suitable safety measures are not taken when installing the devices. In view of this problems, there have been suggested installations wherein the lamps are automatically turned off when people are present in the room.

The known devices therefore suffer from a number of relevant drawbacks, such as a safety degree far from the optimum, installation and space problems, limited effectiveness when compared to the size, that forbid a wide and general spreading.

An object of the present invention is that to overcome the above mentioned drawbacks and inconveniences, and more particularly to realize a safe and effective device of the above kind, having a small size and being transportable or at least easily movable, for sterilising the environment air.

SUMMARY OF THE INVENTION

The above objects are achieved by means of the invention which consists of a device for sterilising a forced air flow by means of ultraviolet radiations comprising:

a housing having an input and an output opening for the air, provided with reflecting inner surfaces;

at least a low pressure mercury vapor lamp located inside said housing; and means for shielding and absorbing the ultraviolet radiation to prevent their escaping ouside the device.

Additional advantageous features are the subject of the dependent claims.

The invention will now be described with reference to preferred embodiments thereof, together with the attached drawings.

BRIEF DESCRIPTION OF THE DRAWINGS

FIG. 1 is a longitudinal cross section of a device according to the invention;

FIG. 3 illustrates a construction of the reflection preventing grid;

FIG. 4 illustrates a preferred embodiment of the shielding and absorbing means;

FIGS. 6 and 7 are a transverse cross section and a front view of a device adapted for the use with an air conditioning plant and FIG. 8 is a schematic longitudinal sectional view of an embodiment of the invention using fins in the form of undulating wave-like sheets.

DESCRIPTION OF PREFERRED EMBODIMENTS

Figure 2:
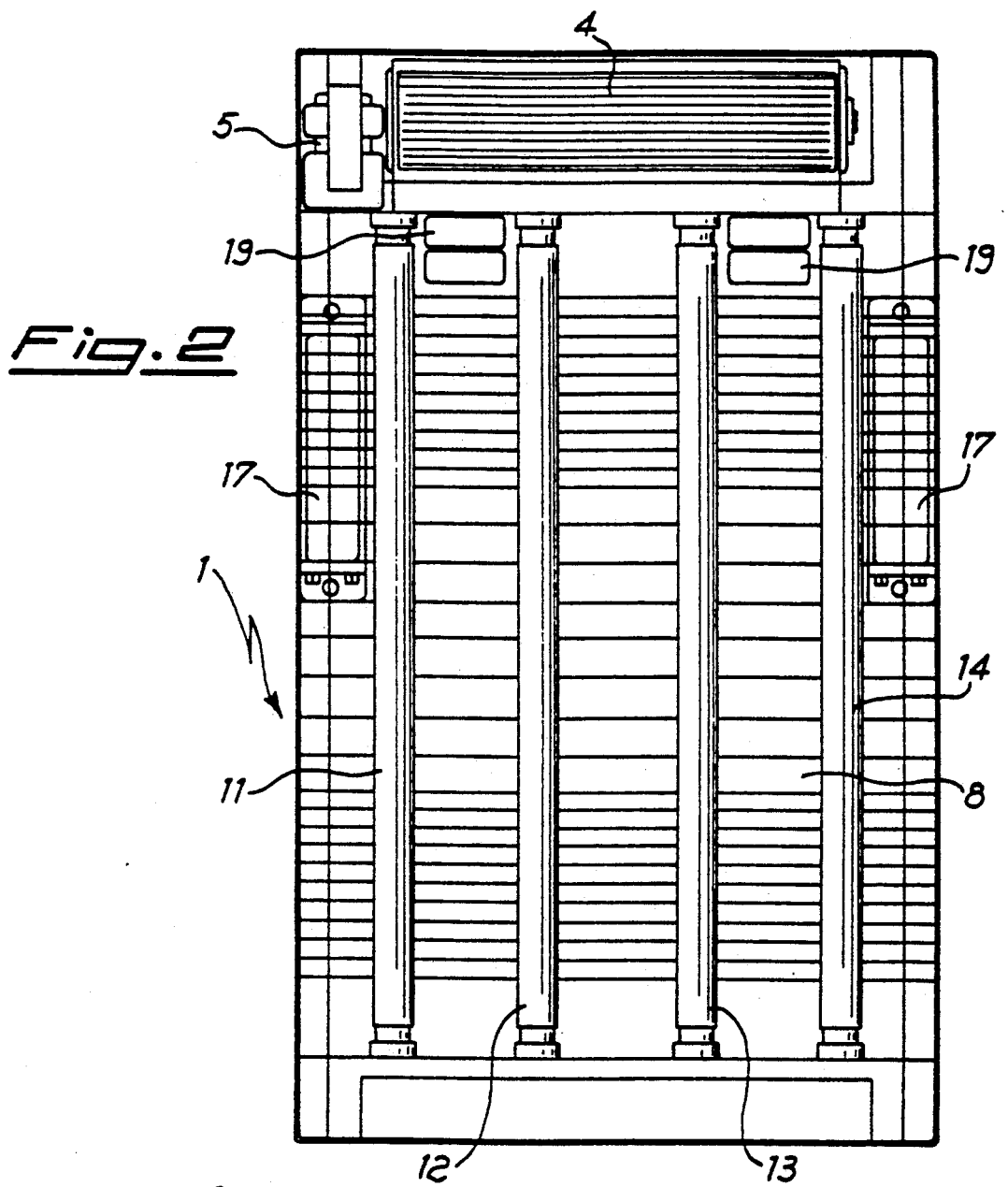
FIG. 2 is a top view of the device of FIG. 1, in a different scale and with the upper cover removed.

With reference to FIGS. 1 and 2, the device according to the invention comprises a housing 1 having a flat parallelepipedic shape wherein the opposed inner surfaces 2 and 3 are reflecting, preferably thanks to an applied layer of reflecting material, e.g. aluminum.

Within the housing there are located four low pressure mercury vapor lamps 11, 12, 13 and 14 that are positioned parallel to each other in the upper portion of the housing 1, in such a way as to define an underlaying free space 7 or passage for the flow of the air to be sterilised. Between the lamps 11-14 and the passage 7 a shield grid 8 is provided the construction of which will be illustrated later with more details. The lamps 11-14, of a type adapted to emit UV - C ultraviolet radiations, are fed in a known manner through reactors 17 and starters 19 shown in FIG. 2.

A fan 4 rotated by an electric motor 5 is located at one end of the housing 1, and is adapted to suck air from the surrounding environment through an arcuate grid 6 and to introduce it into passage 7 with a slight overpressure. At the other end of the housing 1 it is provided a radiused wall 9 and a grid 10 for the output of the sterilised air from the device. Preferably, the inner surface of such wall is dark to prevent the impinging ultraviolet radiation from being reflected. The radiused wall further accomplishes a damping action and allows the emission of the sterilised air quietly and without vortices.

Between the lamps 11-14 and the passage 7 there is provided a grid 8 with parallel fins 20 that are orthogonal to the reflecting surfaces 2, 3. Such fins reduce the output angle of the ultraviolet radiation impinging onto the lower reflecting surface, thus substantially preventing the radiation from getting outside the device. Preferably, the pitch, i.e. the spacing between two adiacent fins, is not constant. As shown in FIGS. 1, 2 and 3 the fins can be closer together at the device's ends and more spaced apart (that is with lower losses of the radiation) in the middle portion.

A preferred embodiment of the grid is shown in FIG. 3. The grid is formed by die cutting a metal thin sheet 22, e.g. an aluminum foil, in order to form the fins 20A and 20B that are then folded at about 90°. Also by folding, from the peripheral portion of sheet 22 a supporting frame is obtained for properly positioning the grid within the device. Alternatively, the grid can be formed by molding a plastic material that is rigid enough and able to resist the ultraviolet radiation. Also the inclination of the fins with respect to the reflecting walls 2 and 3 can be different from 90°.

With reference to the embodiment shown in FIG. 1, at the input and output ends of passage 7 there are formed two tunnels 15 and 16, respectively. Tunnel 15 has horizontal walls 23A and 24A and vertical walls 25A and 26A that are black and further absorb the ultraviolet radiation that might escape the shielding action of grid 8, thus preventing the reflection thereof outside. Tunnel 16 has a similar construction with walls 23B, 24B, 25B and 26B.

According to the invention, the pitch and the inclination of the grid define the maximum angle of incidence, and hence of reflection, of the ultraviolet radiation onto the reflecting walls 2 and 3, and the tunnel lenght is enough to prevent the leakage outside of the reflected beams by intercepting them. This arrangement is quite of advantage since it stops the light without introducing an appreciable resistance to the air flow, so that the fan requires a minimum power and is noiseless.

The fan 4 is preferbly of the tangential type which allows for a good flow rate and is quite noiseless. As an alternative two or more axial fans placed side by side can be used to obtaining a greater (pressure) head.

Figure 5:
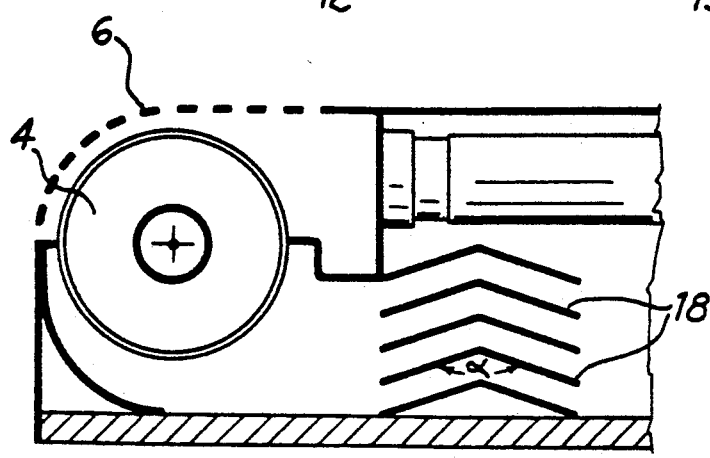
FIG. 5 illustrates another embodiments of the shielding and absorbing means.

A preferred embodiment of the invention with a very reduced size is schematically illustrated in the fragmentary cross section view of FIG. 5, in which the same numeral references of the preceding Figures have been used for marking equal or substantially equivalent components.

Figure 8:
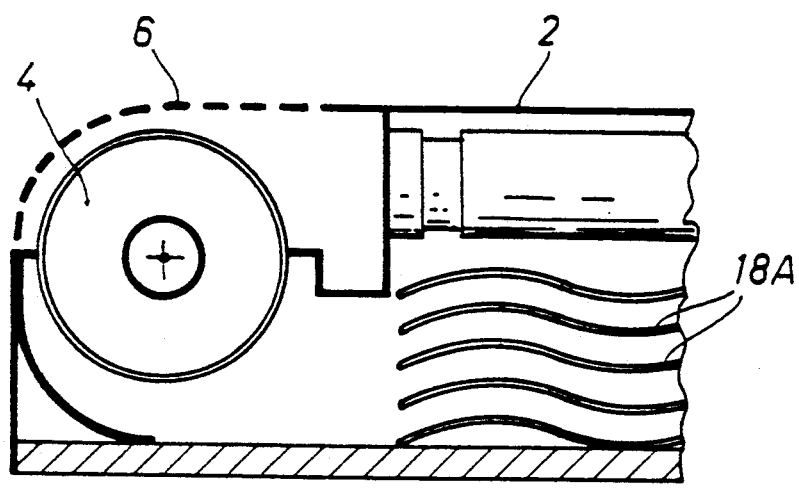

According to this embodiment, at the input end of the device there is arranged a sort of "optical labyrinth" formed by a plurality of superimposed and spaced fins 18 of e.g. a metal sheet or plastic materials. Such fins 18 have an angled shape, like a much opened V, so as to prevent the leakage of ultraviolet radiation. The five fins 18 shown in FIG. 5 are folded to form an obtuse angle $\alpha$ in the order of 150°. It is possible to reduce the number of the fins (and correspondingly decreasing the value of angle $\alpha$), as well as to provide for fins comprising more than two portions connected together, both with an angled and rounded connecting edge, or in the form of undulating wave-like sheets 18A (see FIG. 8). This embodiment is quite advantageous since it provides for a complete shielding of the ultraviolet radiation without introducing an appreciable drag to the air flow, so that the power of the fan 4 is minimized thus diminishing the cost of the device and improving the quiteness thereof. Moreover this construction allows for housing the lamps above the labyrinth in such a way as to further reduce the device length.

According to a further embodiment of the invention, schematically illustrated in the fragmentary cross section of FIG. 4, the optical labyrinth is formed by (at least) a pair of facing walls 30, 31 that are parallel and offset in respect to each other, thus forming a sort of devious path to the beams striking the inner surfaces. A similar pair of walls (not shown) is provided at the output end of the device. The lamps 11-14 are located between the two pairs of walls and an upper shield grid is no longer required, thus reducing the overall height of the device.

The number and the locations of the walls at each housing ends can be selected in different ways, so as to form true labyrinth paths, of course taking into account the fan power.

In the embodiment shown in FIGS. 6 and 7, the device according to the invention is designed to be applied to the output duct 45 of an air conditioning plant, e.g. opening in a room wall 46.

In this embodiment, the housing 40 is relatively short and accomodates three lamps 41, 42 and 43 transversally positioned with respect to the air flow and a single labyrinth of fins 48 parallel and spaced in respect to each other at the input opening of the device. The inner surface 49 of the housing 40 is black or dark coated in order to absorb most of the impinging ultraviolet radiation. Moreover a fan is no longer provided for since the air flow is obtained from the forced air outcoming from the plant.

I claim:

1. A device for sterilising a forced air flow by means of ultraviolet radiations comprising:
   a housing having input and output openings for the air and provided with reflecting inner surfaces;
   a low pressure mercury vapor lamp located inside said housing; and
   an optical labyrinth with a plurality of parallel and spaced sheets defining paths for the air flow and shielding and absorbing the ultraviolet radiation to prevent the escaping thereof outside the device.

2. A device as claimed in claim 1, wherein said sheets are angled fins shaped as a much opened V.

3. A device as claimed in claim 1, wherein said sheets are in form of undulated wave-like sheets.

4. A device as claimed in claims 1 to 3, wherein said housing is elongated and provides for a tangential fan with a protection grid for sucking air into the device and sending it outside after being subjected to an ultraviolet radiation in a flow passage.

5. A device as claimed in claim 4, wherein the axis of said at least one mercury vapor lamp is aligned with the direction of the air flow.

6. A device as claimed in claim 5 further providing for an output radiused wall having a non-reflecting surface and an output grid.

7. A device as claimed in claims 1 to 3 wherein said input opening is adapted for fitting the outlet of an air conditioning plant, and said optical labyrinth is located on the output side of the device.

8. A device as claimed in claim 7 wherein the axis of said at least one mercury vapor lamp is transversely disposed with respect to the direction of the air flow.

9. A device as claimed in claim 1 wherein said input opening is adapted to be fitted to the outlet of an air conditioning plant, and said shielding and absorbing means comprises an optical labyrinth with a plurality of angled fins, parallel and spaced in respect to each other, at the output end of the device.

* * * * *